(12) United States Patent
Van Der Heide et al.

(10) Patent No.: US 12,234,204 B2
(45) Date of Patent: Feb. 25, 2025

(54) PROCESS FOR THE SEPARATION OF GLYCOLS

(71) Applicant: TECHNIP ENERGIES FRANCE SAS., Nanterre (FR)

(72) Inventors: Evert Van Der Heide, Amsterdam (NL); Pieter Huizenga, Amsterdam (NL); Kai Jürgen Fischer, Amsterdam (NL); Carmelo Perez Golf, Amsterdam (NL); David Pinilla Garcia, Amsterdam (NL)

(73) Assignee: TECHNIP ENERGIES FRANCE SAS., Nanterre (FR)

( * ) Notice: Subject to any disclaimer, the term of this patent is extended or adjusted under 35 U.S.C. 154(b) by 337 days.

(21) Appl. No.: 17/776,268

(22) PCT Filed: Dec. 16, 2020

(86) PCT No.: PCT/EP2020/086583
§ 371 (c)(1),
(2) Date: May 12, 2022

(87) PCT Pub. No.: WO2021/122853
PCT Pub. Date: Jun. 24, 2021

(65) Prior Publication Data
US 2022/0388933 A1 Dec. 8, 2022

(30) Foreign Application Priority Data

Dec. 16, 2019 (EP) ..................................... 19216694

(51) Int. Cl.
*C07C 29/84* (2006.01)
(52) U.S. Cl.
CPC .................................. *C07C 29/84* (2013.01)

(58) Field of Classification Search
CPC ....... C07C 29/84; C07C 31/22; C07C 31/205; C07C 31/207; C07C 31/20; C07C 31/225
See application file for complete search history.

(56) References Cited

U.S. PATENT DOCUMENTS

| 4,966,658 A | 10/1990 | Berg |
| 5,423,955 A | 6/1995 | Berg |

(Continued)

FOREIGN PATENT DOCUMENTS

| CN | 102372600 A | 3/2012 |
| CN | 102643165 A | 8/2012 |

OTHER PUBLICATIONS

International Search Report and Written Opinion received for PCT Patent Application No. PCT/EP2020/086583, mailed on Mar. 23, 2021, 8 pages.

(Continued)

*Primary Examiner* — Jafar F Parsa
(74) *Attorney, Agent, or Firm* — Troutman Pepper Locke LLP; Christopher J. Capelli; Nicholas J. DiCeglie, Jr.

(57) ABSTRACT

A process for the production of a high purity first diol from a product stream comprising two or more C2 to C7 diols, said process comprising the steps of: (i) providing the product stream to a first distillation column; (ii) providing an extractant selected from the group of C3 to C6 sugar alcohols and mixtures thereof to the first distillation column; (iii) operating the first distillation column to obtain a first bottoms stream comprising at least a first diol and the extractant; (iv) providing the first bottoms stream to a second distillation column operating to obtain a second top stream comprising the first diol and diols with atmospheric boiling points at least 10° C. higher than the first diol, and (v) providing the second top stream to a third distillation column to obtain a third top stream comprising the first diol; wherein the product stream comprises 0.1 to 10 wt % of (Continued)

diols with atmospheric boiling points at least 10° C. higher than the first diol, calculated upon the total weight of C2 to C7 diols in the product stream.

11 Claims, 3 Drawing Sheets

(56) References Cited

U.S. PATENT DOCUMENTS

| | | |
|---|---|---|
| 10,752,567 B2 | 8/2020 | Muthusamy et al. |
| 11,198,664 B2 | 12/2021 | Jackson et al. |
| 11,384,039 B2 | 7/2022 | Fischer et al. |
| 2011/0312050 A1 | 12/2011 | Zhang et al. |
| 2017/0174596 A1 | 6/2017 | Huizenga et al. |
| 2019/0062244 A1 | 2/2019 | Perez Golf et al. |
| 2019/0202764 A1 | 7/2019 | Fischer et al. |

OTHER PUBLICATIONS

Office Action Received for Chinese Application No. 202080087183.9, Mailed on Apr. 29, 2023, 16 Pages (10 Pages of English Translation and 6 Pages of Official Copy).

PROCESS FOR THE SEPARATION OF GLYCOLS

CROSS REFERENCE TO RELATED APPLICATIONS

This is a National stage application of International application No PCT/EP2020/086583, filed Dec. 16, 2020, which claims priority of EP application Ser. No. 19/216,694.0, filed Dec. 16, 2019, which is incorporated herein by reference in its entirety.

TECHNICAL FIELD

The present disclosure relates to a process for the selective separation of glycols.

BACKGROUND

Glycols and in particular ethylene glycol and propylene glycol are valuable materials with a multitude of commercial applications, e.g. as heat transfer media, antifreeze, and precursors to polymers, such as PET. Most glycols are prepared by industrial routes from petrochemicals derived from crude oil. For example, ethylene and propylene glycols are typically made on an industrial scale by hydrolysis of the corresponding alkylene oxides, which are the oxidation products of ethylene and propylene, produced from fossil fuels.

In recent years, increased efforts have focused on producing chemicals, including glycols, from renewable feedstocks, such as sugar-based materials. For example, US20110312050 describes a continuous process for the catalytic generation of polyols from cellulose, in which the cellulose is contacted with hydrogen, water and a catalyst to generate an effluent stream comprising at least one polyol.

CN102643165 is directed to a catalytic process for reacting saccharides in an aqueous solution with hydrogen in the presence of a catalyst in order to generate polyols.

As with many chemical processes, the reaction product stream in these reactions comprises a number of desired materials, diluents, by-products and other undesirable materials. In order to provide a high value process, the desirable product or products must be obtainable from the reaction product stream in high purity with a high percentage recovery of each product and with as low as possible use of energy and complex equipment.

In known processes to make glycols, the glycols are usually present at high dilution in a solvent, typically water. The water is usually removed from the glycols by distillation. Subsequent purification of the glycols is then carried out by fractional distillation. This process can have high costs both in terms of capital and operational expenditure. Further, repeated heating or maintenance at raised temperatures in the fractional distillation steps may also lead to decomposition of the desired glycol products.

When glycols are produced by hydrogenolysis of saccharides, a mixture of diols, including glycols and other by-products is produced. The main glycol constituents in the reaction product stream are monoethylene glycol (MEG), monopropylene glycol (MPG) and 1,2-butanediol (1,2-BDO). Other diols, such as 2,3-butanediol (2,3-BDO), pentanediols, hexanediols and heptanediols may also be present. The separation of these diols by fractional distillation is complicated due to the similarity in boiling points. For example, MEG and 1,2-BDO have normal boiling points of 197.2 and 196.5° C., respectively. Further, the isolation of a pure MEG overheads stream by fractional distillation from a mixture comprising MEG and 1,2-BDO is made impossible by the formation of a homogeneous minimum boiling azeotrope between MEG and 1,2-BDO at atmospheric pressure. A similar close-boiling, azeotrope-forming glycol pair is MPG and 2,3-pentanediol. Other close boiling and/or azeotropic mixtures may also be formed between other diols present, further complicating the purification process.

Degradation of the products at high temperatures makes the use of higher than atmospheric pressure for distillation less desirable.

Methods to separate diols and, in particular, 1,2-BDO and MEG have been described in the art.

U.S. Pat. No. 4,966,658 is directed to the separation of a mixture of 1,2-BDO and MEG using a process known as azeotropic distillation in which an azeotrope-forming agent is added to the mixture before distillation in order to facilitate separation. Suitable azeotrope-forming agents are stated to include 3-heptanone, o-xylene, cumene and heptane. A similar process is described in U.S. Pat. No. 5,423,955 for the separation of 1,2-BDO and MPG, in this case using (among others) toluene, o-xylene, cumene and heptane as azeotrope-forming agents. Azeotropic distillation can lead to an increase in relative volatility between the components but also leads to further process steps in order to remove the azeotrope forming agents.

CN102372600 describes an extractive distillation process for the separation of glycols. In this process, a mixture of MEG, MPG and 1,2-BDO are fed to a distillation column and contacted therein with an extractant. The top product, comprising the light extractant and 1,2-BDO, is then separated in a further distillation column. The bottom product, comprising MEG, MPG and extractant is subjected to further distillation to provide MEG as the bottoms product. Suitable extractants are stated to include C6-C9 aromatics, alkanes, alkenes, C6-C11 ketones or ethers with toluene, o-xylene, cumener, n-heptane, n-octane, 3-heptanone and diethylene glycol dimethyl ether mentioned as preferred extractant. This teaching appears to be somewhat inconsistent with the above cited cases, which name the materials as azeotrope-forming agents.

WO2015150520 discloses a process for separating monoethylene glycol from a mixture comprising monoethylene glycol and 1,2-butanediol, using a two column, pressure-swing distillation set-up.

WO2017050847 discloses a simple and efficient method suitable for the recovery of desired diol products, such as MEG or MPG, from a mixture of diols from a product stream derived from a saccharide hydrolysis process or other bio-based processes. In the examples in WO2017050847 no 1,2 HDO, or only 0.01 wt % 1,2 HDO, was present in the feed to the extractive distillation column. Components such as 1,2 hexanediol were separated in a first distillation column together with high boiling components in the bottoms stream of the first distillation column, before extractive distillation. Such separation of 1,2-HDO in this first distillation column, however, requires a relatively large amount of energy, and requires relatively large equipment.

A related disadvantage is the need for multiple separation steps and/or multiple trays in a distillation before the extractive distillation. Another related disadvantage is that a part of the desired diol product, such as MEG or MPG, may end up in the bottoms stream together with components such as 1,2 hexane diol in the distillation before the extractive distillation; this especially when a relatively low bottom temperature is used. Another related disadvantage is that degradation products may be formed; this especially when a relatively high bottom temperature is used during the distillation before the extractive distillation. The operability of such a first distillation thus is lower than desired.

Hence, recovery of desired diol products, such as MEG or MPG, from a mixture of diols from a product stream derived from a saccharide hydrolysis process or other bio-based processes thus far encountered problems with close-boiling components and/or by-products and with azeotrope forming components and/or by-products, resulting in complex procedures and/or energy demanding procedures and/or contaminated end products.

It would be advantageous to provide a simple and efficient method suitable for the recovery of desired diol products, such as MEG or MPG, from a mixture of diols from a product stream derived from a saccharide hydrolysis process or other bio-based processes.

SUMMARY

Accordingly, the present disclosure provides a process for the production of a high purity first diol, selected from the group consisting of C2 to C7 diols from a product stream comprising two or more C2 to C7 diols, said process comprising the steps of:
 (i) providing the product stream to a first distillation column;
 (ii) providing an extractant selected from the group of C3 to C6 sugar alcohols and mixtures thereof to the first distillation column;
 (iii) operating the first distillation column at a temperature in the range of from 50 to 250° C. and a pressure in the range of from 0.1 to 400 kPa to obtain a first bottoms stream comprising at least a first diol and the extractant and a first top stream comprising a mixture comprising one or more C2 to C7 diols;
 (iv) providing the first bottoms stream to a second distillation column operating at a temperature in the range of from 50 to 250° C. and a pressure in the range of from 0.1 to 400 kPa to obtain a second top stream comprising the first diol and diols with atmospheric boiling points at least 10° C. higher than the first diol, and
 (v) providing the second top stream to a third distillation column to obtain a third top stream comprising the first diol in a purity higher than 99.5% by weight; wherein the product stream comprises 0.1 to 10 wt % of diols with atmospheric boiling points at least 10° C. higher than the first diol, calculated upon the total weight of C2 to C7 diols in the product stream.

Additional features, advantages, and embodiments of the disclosed subject matter may be set forth or apparent from consideration of the following detailed description, drawings, and claims. Moreover, it is to be understood that both the foregoing summary and the following detailed description are examples and are intended to provide further explanation without limiting the scope of the claims.

The current process does not have problems with close-boiling components and/or by-products and with azeotrope forming components and/or by-products. This because close-boiling components and/or by-products can be more easily removed from the extractant (for example glycerol) as compared to removal from MEG or MPG. And azeotropes are not formed in the extractive distillation.

Furthermore, as compared to the processes of the examples of WO2017050847, the current process does not require removing components such as 1,2 hexanediol from a MEG or MPG comprising product stream before the extractive distillation. Hence, significantly less energy is required is required when removing high boiling components before the extractive distillation, and less or smaller equipment can be used. Separation of diols with atmospheric boiling points at least 10° C. higher than the first diol (for example 1,2 hexanediol) from the first diol (e.g. MEG or MPG) does not require a lot of energy. The overall energy required for the process of the present invention is lower than the overall energy required for a process as described in the examples of WO2017050847. Additionally, glycerol produced in the hydrogenolysis of saccharides may remain in a MEG or MPG comprising product stream. The presence of glycerol in the MEG or MPG mixture may reduce or eliminate any glycerol make-up as compensation for a possible glycerol bleed from the glycerol recycle in the extractive distillation.

In the process provided by the present disclosure, preferably the product stream is subjected to rotary evaporation, flashing, and/or by separation using 1 to 10 trays, preferably by separation using 2 to 9 trays, more preferably by separation using 3 to 5 trays, to remove high boiling components prior to step (i). Separation using 1 to 10 trays, 2 to 9 trays or 3 to 5 trays may also be referred to as distillation using 1 to 10 trays, 2 to 9 trays or 3 to 5 trays. Separation using 1 to 10 trays, 2 to 9 trays or 3 to 5 trays may also be referred to as flashing using 1 to 10 trays, 2 to 9 trays or 3 to 5 trays.

Preferably the first diol is MEG and the product stream comprises at least MEG and 1,2-BDO, wherein the product stream provided to step (i) preferably has a weight ratio of MEG:1,2-BDO of at least 5:1. In another preferred embodiment the first diol is MPG and the product stream comprises at least MPG and 2,3-pentanediol. Preferably the product stream is, or is derived from, a product stream of a saccharide hydrogenolysis process. Preferably one or more sugar alcohols, preferably glycerol, is present in the product stream used in step (i).

The product stream may comprise a solvent. This may be removed prior to step (i) to provide a solvent-lean product stream. The solvent may be water or a C1 to C6 alcohol or polyalcohol or mixtures thereof. Preferably the product stream comprises at least MEG and 1,2-BDO and a solvent, and prior to step (i) the solvent is removed from the product stream to provide a solvent-lean product stream.

Preferably a second bottoms stream comprising a used extractant stream is also obtained in step (iv). More preferably at least a first portion of the second bottoms stream comprising the used extractant is recycled to the first distillation column as at least a portion of the extractant.

Preferably the extractant is added in an amount such that the weight ratio of the extractant to the product is at least 0.25:1 and at most 10:1 based on the overall weight of the feed/mixture.

Preferably at least a second portion of the second bottoms stream comprising the used extractant and the at least first diol is provided to a fourth distillation column to obtain a fourth top stream comprising the first diol and a fourth bottoms stream comprising the used extractant, both of which are recycled to the first distillation column.

Preferably a finishing section is added to the top of the third distillation column above the point at which the high purity first diol stream is obtained, in order to remove any type of light impurities/light degradation products formed in the separation process, preferably by hydrogenation.

DETAILED DESCRIPTION

The following description of the variations is merely illustrative in nature and is in no way intended to limit the scope of the disclosure, its application, or uses. The description and examples are presented herein solely for the purposes of illustrating the various embodiments of the disclosure and should not be construed as a limitation to the scope and applicability of the disclosure.

The terminology and phraseology used herein is for descriptive purposes and should not be construed as limiting in scope. Language such as "including," "comprising," "having," "containing," or "involving," and variations thereof, is intended to be broad and encompass the subject matter listed thereafter, equivalents, and additional subject matter not recited.

Also, as used herein any references to "one embodiment" or "an embodiment" means that a particular element, feature, structure, or characteristic described in connection with the embodiment is included in at least one embodiment. The appearances of the phrase "in one embodiment" in various places in the specification are not necessarily referring to the same embodiment.

The present inventors have determined a new method for the production of a high purity diol from a product stream. The product stream may be derived from a saccharide hydrogenolysis process. Such a product stream from a process for the hydrogenolysis of a saccharide-containing feedstock comprises certain desirable diols as well as by-products comprising diols and other materials.

The product stream comprises two or more C2 to C7 diols. In some embodiments, the two or more C2 to C7 diols, including a first diol, are selected from the group consisting of C2 to C7 glycols. The term glycol as used herein is given its usual meaning, i.e. a diol in which the two hydroxyl groups are present on vicinal carbon atoms. In some embodiments, the first diol is monoethylene glycol (MEG) and the product stream comprises MEG and 1,2-butanediol (1,2-BDO), or the first diol is monopropylene glycol (MPG) and the product stream comprises MPG and 2,3-pentanediol.

In some embodiments, the process for the production of a high purity first diol, selected from the group consisting of C2 to C7 diols from a product stream comprising two or more C2 to C7 diols, includes the steps of:
(i) providing the product stream to a first distillation column;
(ii) providing an extractant selected from the group of C3 to C6 sugar alcohols and mixtures thereof to the first distillation column;
(iii) operating the first distillation column at a temperature in the range of from 50 to 250° C. and a pressure in the range of from 0.1 to 400 kPa to obtain a first bottoms stream comprising at least a first diol and the extractant and a first top stream comprising a mixture comprising one or more C2 to C7 diols;
(iv) providing the first bottoms stream to a second distillation column operating at a temperature in the range of from 50 to 250° C. and a pressure in the range of from 0.1 to 400 kPa to obtain a second top stream comprising the first diol and diols with atmospheric boiling points at least 10° C. higher than the first diol, and
(v) providing the second top stream to a third distillation column to obtain a third top stream comprising the first diol in a purity higher than 99.5% by weight;
wherein the product stream comprises 0.1 to 10 wt % of diols with atmospheric boiling points at least 10° C. higher than the first diol, calculated upon the total weight of C2 to C7 diols in the product stream.

In some embodiments, the product stream is, or is derived from, a reaction product stream from a process for the hydrogenolysis of a saccharide-containing feedstock, which as well as diols will also contain a solvent. In this embodiment, prior to subjecting the product stream to distillation in the first distillation column, the product stream may be subjected to solvent removal, e.g. by distillation, in order to provide a solvent-lean product stream.

Typically, the reaction product stream from a process for the hydrogenolysis of a saccharide-containing feedstock comprises, as diols, at least MEG, MPG and 1,2-BDO. Other diols, such as 2,3-BDO, pentanediols, hexanediols and heptanediols may also be present. These diols are typically present at a concentration in the range of from 0.1 to 50 wt % of the overall reaction product stream.

In such a reaction product stream, MEG is suitably present as at least 10 wt %, sometimes as at least 30 wt % of the non-solvent fraction of the stream. MEG is suitably present as at most 95 wt %, sometimes as at most 90 wt %, and sometimes as at most 80 wt % of the non-solvent fraction of the stream.

In such a reaction product stream, MPG is suitably present as at least 2 wt %, sometimes as at least 4 wt % of the non-solvent fraction of the stream. MPG is suitably present as at most 70 wt %, sometimes as at most 45 wt %, sometimes as at most 20 wt % of the non-solvent fraction of the stream.

In such a reaction product stream, 1,2-BDO is typically present as at least 1 wt %, generally as at least 4 wt % of the non-solvent fraction of the stream. 1,2-BDO is suitably present as at most 20 wt %, sometimes as at most 8 wt % of the non-solvent fraction of the stream.

The presently claimed process allows for the product stream to comprise 0.1 to 10 wt % of diols with atmospheric boiling points at least 10° C. higher than the first diol, which first diol preferably is MEG or MPG, calculated upon the total weight of C2 to C7 diols in the product stream.

An example of a diol with an atmospheric boiling point at least 10° C. higher than the first diol is 1,2 hexanediol.

Also one or more sugar alcohols, preferably glycerol, may be present in the product stream used in step (i). For example, sugar alcohol(s) produced in the hydrogenolysis of saccharides may remain in a MEG or MPG comprising product stream. One or more sugar alcohols, preferably glycerol, may be used as extractant. The presence of sugar alcohol(s) in the product stream used in step (i), which may comprise MEG or MPG, may reduce or eliminate any sugar alcohol make-up as compensation for a possible sugar alcohol bleed from the sugar alcohol recycle in the extractive distillation.

The product stream used in step (i) comprises at least 0.1 wt % of diols with atmospheric boiling points at least 10° C. higher than the first diol, calculated upon the total weight of C2 to C7 diols in the product stream. It may comprise at least 0.2 wt %, or at least 0.5 wt % diols with atmospheric boiling points at least 10° C. higher than the first diol, calculated upon the total weight of C2 to C7 diols in the product stream. The product stream used in step (i) comprises at most 10 wt % of diols with atmospheric boiling points at least 10° C. higher than the first diol, calculated upon the total weight of C2 to C7 diols in the product stream. It may comprise at most 7 wt %, or at most 5 wt % or at most 3 wt % diols with atmospheric boiling points at least 10° C. higher than the first diol, calculated upon the total weight of C2 to C7 diols in the product stream.

The product stream used in step (i) comprises 0.1 to 10 wt % of diols with atmospheric boiling points at least 10° C. higher than the first diol. These diols preferably are or comprise aliphatic diols, more preferably are or comprise aliphatic C2 to C7 diols, even more preferably is or comprise 1,2 hexanediol.

The hydrogenolysis reaction is carried out in the presence of a solvent. Therefore, the reaction product stream will also contain said solvent. The solvent may be water or a C1 to C6 alcohol or polyalcohol (including sugar alcohols) or mixtures thereof. Examples of C1 to C6 alcohols include methanol, ethanol, 1-propanol and iso-propanol. Polyalcohols of use include glycols, particularly products of the hydrogenation/hydrogenolysis reaction, glycerol, erythritol, threitol, sorbitol and mixtures thereof. In some embodiments, the solvent comprises water.

As well as the C2 to C7 diols and the solvent, the reaction product streams from hydrogenolysis reactions of saccharides may comprise oxygenates, hydrocarbons, catalyst, degradation products, and gases in any composition. The variety of compounds and their concentration depend on the saccharide-containing feedstock and the various hydrogenation and hydrogenolysis conversion conditions, including catalysts, reaction conditions such as temperature, pressure and saccharide concentration. However, suitably the hydrogenolysis reactions have gone to completion and the aqueous stream contains less than 5 wt %, sometimes less than 2 wt %, sometimes less than 1 wt %, sometimes less than 0.5 wt %, sometimes substantially no saccharides when considered as a weight percentage of the overall stream. If the solvent used comprises water or a C1 to C6 alcohol typically, the reaction product stream also contains less than 5 wt %, sometimes less than 2 wt %, sometimes less than 1 wt %, sometimes less than 0.5 wt %, sometimes substantially no glycerol, when considered as a weight percentage of the overall stream.

In embodiments of the process, solvent, for example water, may be removed from the product stream, e.g. by distillation, prior to subjecting the product stream to distillation in the first distillation column. In this embodiment, the solvent removal may be carried out in a single distillation column. In some embodiments, it is carried out over a number of distillation steps, for example by multi-effect evaporation or a combination of multi-effect evaporation and solvent removal (e.g. dehydration) by distillation.

In some embodiments, the solvent present in the reactor is removed to provide a solvent-lean product stream. The term 'solvent-lean' used herein refers to the fact that the product stream is essentially solvent free. In practice, a small amount of solvent may be present in the solvent-lean product stream within the scope of the disclosure. If the solvent comprises water or a C1 to C6 alcohol, sometimes no more than 1000 ppmw, sometimes no more than 400 ppmw, sometimes no more than 200 ppmw, sometimes no more than 100 ppmw of solvent is present in the solvent-free product stream. If a polyalcohol, such as a sugar alcohol is used as the solvent, a higher amount of the solvent may be tolerated in the 'solvent-lean' product stream.

Other steps, such as removal of light ends or filtration off of a heterogeneous catalyst, may also be applied to the product stream upstream or downstream of the step of removing the solvent. Heavy (high boiling) by-products may be separated from the product stream upstream or downstream of the step of removing the solvent. In case of separation of high boiling components, heterogeneous catalyst may be removed at the same time. The use of such steps will depend on the conditions and/or composition of the reaction mixture in the saccharide hydrogenolysis process. One option is to remove light alcohols, followed by removing water, followed by removing high boiling components and/or catalyst.

In the process provided by the present disclosure, the product stream provided to the first (extractive) distillation column in step (i) comprises 0.1 to 10 wt % of diols with atmospheric boiling points at least 10° C. higher than the first diol, calculated upon the total weight of C2 to C7 diols in the product stream. Preferably the product stream is subjected to rotary evaporation, flashing, and/or by separation using 1 to 10 trays, preferably by separation using 2 to 9 trays, more preferably by separation using 3 to 5 trays, prior to step (i), to remove high boiling components, and optionally also to remove catalyst. Diols with atmospheric boiling points at least 10° C. higher than the first diol may remain in the product stream in an amount of 0.1 to 10 wt %, calculated upon the total weight of C2 to C7 diols in the product stream.

The product stream, or the solvent-lean product stream, from which light ends and/or catalyst and/or high boiling components may have been removed, is provided to a first distillation column to obtain a first bottoms stream and a first top stream. Also provided to the first distillation is an extractant, which can be fed at a position above, at or below the feed entry point, or distributed over the column. In some embodiments, the extractant is introduced above the point at which the product stream is provided. In another embodiment, a divided wall distillation column can be applied where the extractant can be supplied opposite to the feed entry point or provided at multiple entry points. In some embodiments, the extractant is provided at the top of or a few stages below the top of the first distillation column. The first top stream is removed from the first distillation column above the point at which the extractant is provided to the first distillation column. The first top stream may comprise a mixture comprising one or more C2 to C7 diols, sometimes referred to as light glycols. The term "light glycols" refers to diols having boiling points lower than or equal to MEG or less than 10° C. higher than MEG. In the separation of MEG and 1,2-BDO, this first top stream would comprise 1,2-BDO; and in the separation of MPG and 2,3-pentanediol, this stream would comprise 2,3-pentanediol. In some embodiments, the first top stream is removed from the first distillation column as a condensed overheads stream. The first top stream may contain other diols such as 2,3-BDO and heptanediols. In the separation of MEG and 1,2-BDO the first top stream may also contain MPG. In some embodiments, the first top stream may be subjected to one or more fractional distillation steps in order to produce desired products as pure product streams.

The extractant is selected from the group of C3 to C6 sugar alcohols and mixtures thereof. Sugar alcohols have the general formula $HOCH_2(CHOH)_nCH_2OH$. Suitable sugar alcohols include glycerol, erythritol, threitol, arabitol, xylitol, ribitol, mannitol, sorbitol, galacticol and iditol. Although some of these sugar alcohols may be solid at room temperature, pressures and compositions for suitable extractant mixtures, they can be used as liquids at suitable temperatures and pressures in embodiments of the disclosed process.

In some embodiments, the extractant comprises glycerol.

As well as the extractant, this stream may also include trace components including "heavies", such as other polyalcohols, especially other sugar alcohols, from a recycle stream in the process. In some embodiments, this stream may also include glycerol, erythritol, threitol and sorbitol from the hydrogenolysis process. One example of a suitable recycle stream is the bottoms stream comprising high boiling by-products provided in step (ii) of the instant process. Such high boiling by-products will include C3-C6 sugar alcohols. In some embodiments, at least a portion of said bottoms stream may be used as at least a portion of the extractant, and in other embodiments after distillation to remove the heaviest portion of said bottoms stream.

In some embodiments, the extractant is added in an amount such that the weight ratio of the extractant to the product stream is at least 0.05:1, sometimes at least 0.1:1, even sometimes at least 0.25:1, based on the overall weight of the feed/mixture. In some embodiments, the weight ratio of the extractant to the product stream is at most 10:1, sometimes at most 5:1, sometimes 2:1, sometimes at most 1.5:1, based on the overall weight of the feed/mixture.

The distillation in the first distillation column is carried out at a temperature in the range of from 50 to 250° C., sometimes from 100 to 200° C. and at a pressure of at least 0.1 kPa. Generally, a pressure of at least 1 kPa is used for economic reasons, with a pressure of at least 5 kPa sometimes used for the same reasons. The pressure is at most 400 kPa, sometimes at most 200 kPa, sometimes at most 120 kPa. It will be clear to the skilled person to vary the temperature and pressure in relation to each other in order to achieve suitable conditions.

The first bottoms stream may comprise at least a first diol, for example MEG or MPG, and the extractant. The first bottoms stream may additionally comprise one or more diol(s) with atmospheric boiling points at least 10° C. higher than the first diol, for example 1,2 hexanediol. In one embodiment, the first diol content of the first bottoms stream, comprises at least 95 wt % of the first diol, sometimes at least 98 wt % of the first diol, sometimes at least 99 wt % of the first diol, sometimes at least 99.5 wt % of the first diol, sometimes at least 99.9 wt % of the first diol, calculated upon the first diol content in the feed to the first distillation column. In one embodiment in which the first diol is MEG, suitably, the diols content of the first bottoms stream, comprises at least 95 wt % MEG, sometimes at least 98 wt % MEG, sometimes ably at least 99 wt % MEG, sometimes at least 99.5 wt % MEG, sometimes at least 99.9 wt % MEG, calculated upon the MEG content in the feed to the first distillation column.

The first bottoms stream is then subjected to a further distillation step in a second distillation column in which the first diol and diols with atmospheric boiling points at least 10° C. higher than the first diol is distilled off to provide a second top stream and a second bottoms stream. The second distillation is carried out at the same or lower pressure than in the extractive distillation step (in the first distillation column) in order to restrict the temperature in the reboiler and avoid or minimize potential product degradation.

The distillation in the second distillation column is carried out at a temperature in the range of from 50 to 250° C., sometimes of from 100 to 200° C. and at a pressure of at least 0.1 kPa. Generally, a pressure of at least 1 kPa is used for economic reasons, with a pressure of at least 5 kPa used for the same reasons. The pressure is at most 400 kPa, sometimes at most 200 kPa, sometimes at most 120 kPa. It will be clear to the skilled person to vary the temperature and pressure in relation to each other in order to achieve suitable conditions.

The first diols content of the second top stream, comprises at least 95 wt % of the first diol, sometimes at least 98 wt % of the first diol, sometimes at least 99 wt % of the first diol, sometimes at least 99.5 wt % of the first diol, sometimes at least 99.9 wt % of the first diol, calculated upon the first diol content in the feed to the second distillation column. In one embodiment in which the first diol is MEG, suitably, the diols content of the second top stream, comprises at least 95 wt % MEG, sometimes at least 98 wt % MEG, sometimes at least 99 wt % MEG, sometimes at least 99.5 wt % MEG, sometimes at least 99.9 wt % MEG, calculated upon the MEG content in the feed to the second distillation column.

The second top stream is then subjected to a further distillation step in a third distillation column in which the first diol (in some embodiments MEG, in some embodiments MPG) is distilled off to provide a high purity first diol stream as a third top stream along with a third bottoms stream. In some embodiments, this distillation is carried out at the same or lower pressure than in the second distillation column in order to restrict the temperature in the reboiler and avoid or minimize potential product degradation.

The second bottoms stream from the second distillation column comprises a used extractant stream. At least a first portion of the second bottoms stream may then be recycled to the first distillation column as at least a portion of the extractant. Any heavies left that had been present in the first mixture (the first mixture preferably comprising MEG and 1,2-BDO, or comprising MPG and 2,3-pentanediol) may also be present in the extractant stream to be recycled. If the mixture comprising two or more C2 to C7 diols and a solvent is derived from the reaction product stream from a process for the hydrogenolysis of a saccharide-containing feedstock, such heavies are likely to be sugar alcohol like in their structure, boiling point and other physical properties and may be recycled with the rest of the extractant stream.

Another portion of the second bottoms stream may be removed as a bleed in order to prevent a build-up of heavies. In this embodiment, fresh extractant will be provided to the first distillation column to make up the required amount of extractant. This fresh extractant should be provided to the first distillation column at the same height or above the second bottoms stream recycle feed position.

The distillation in the third distillation column is carried out at a temperature in the range of from 50 to 250° C., sometimes from 100 to 200° C. and at a pressure of at least 0.1 kPa. Generally, a pressure of at least 1 kPa is used for economic reasons, with a pressure of at least 5 kPa sometimes used for the same reasons. The pressure is at most 400 kPa, sometimes at most 200 kPa, sometimes at most 120 kPa. It will be clear to the skilled person to vary the temperature and pressure in relation to each other in order to achieve suitable conditions.

High purity diol, as used herein in the third top stream, refers to a diol of at least 99 wt % purity, sometimes at least 99.5 wt %, sometimes at least 99.6 wt % purity, sometimes at least 99.9 wt % purity. In some embodiments wherein the first diol is MEG, the high purity MEG is suitable for use as fibre grade MEG. The third bottoms stream comprises diols boiling higher than 10° C. higher than the first diol, as well as any heavy by-product or degradation product formed during the separation process, referred to herein as 'heavy diols'.

Optionally, a finishing section may be added to the top of this third distillation column in order to remove any type of light impurities/light degradation products formed at the separation process. This section would be above the point at which the high purity first diol stream is removed. The finishing section preferably is a hydrogenation section. When any light impurities/light degradation products are hydrogenated, the UV specification of the first diol (preferably MEG or MPG) is more easily met.

In another embodiment, the second bottoms stream from the second distillation column further comprises a portion of the at least first diol not found in the second top stream. In some embodiments, the first portion of the second bottoms stream is sent to the first distillation column and a second portion of the second bottoms stream is sent to a fourth distillation column to recover a fourth top stream comprising the first diol and a fourth bottoms stream comprising the used extractant. Optionally, the first diol, sometimes MEG, stream may be recovered by subjecting the fourth top stream to further processing steps. By utilizing a fourth distillation column, the second distillation column may be operated such that the amount of the first diol in the second top stream may be decreased and will be recovered in the fourth distillation column. By reducing the amount of the first diol in the second top stream, lower energy requirements may be necessary. In some embodiments, when the first diol is MEG, components above MEG and below hexanediol (heavy diols) will not exit with the MEG product but will be recycled and removed/recovered.

The distillation in the fourth distillation column is carried out at a temperature in the range of from 50 to 250° C., sometimes from 100 to 200° C. and at a pressure of at least 0.1 kPa. Generally, a pressure of at least 1 kPa is used for economic reasons, with a pressure of at least 5 kPa sometimes used for the same reasons. The pressure is at most 400 kPa, sometimes at most 200 kPa, sometimes at most 120 kPa. It will be clear to the skilled person to vary the temperature and pressure in relation to each other in order to achieve suitable conditions.

Embodiments will now be further illustrated with reference to non-limiting embodiments shown in the drawings. In the drawings, the first numeral of each reference number refers to the Figure number, e.g. 1XX for FIG. 1, 2XX for FIG. 2, and 3XX for FIG. 3. The remaining figures relate to the individual features within the Figures. The same number is used to refer to the same feature in each Figure. Therefore, 107 refers to the same feature in FIG. 1 as 207 refers to in FIG. 2.

In this description, the separation of high purity MEG from a mixture comprising MEG and 1,2-BDO from a saccharide hydrogenolysis process is described. The same system could be used to separate other mixtures such as MPG and 2,3-pentanediol, or any mixture of diols from a product stream comprising two or more C2 to C7 diols.

Figure 1:
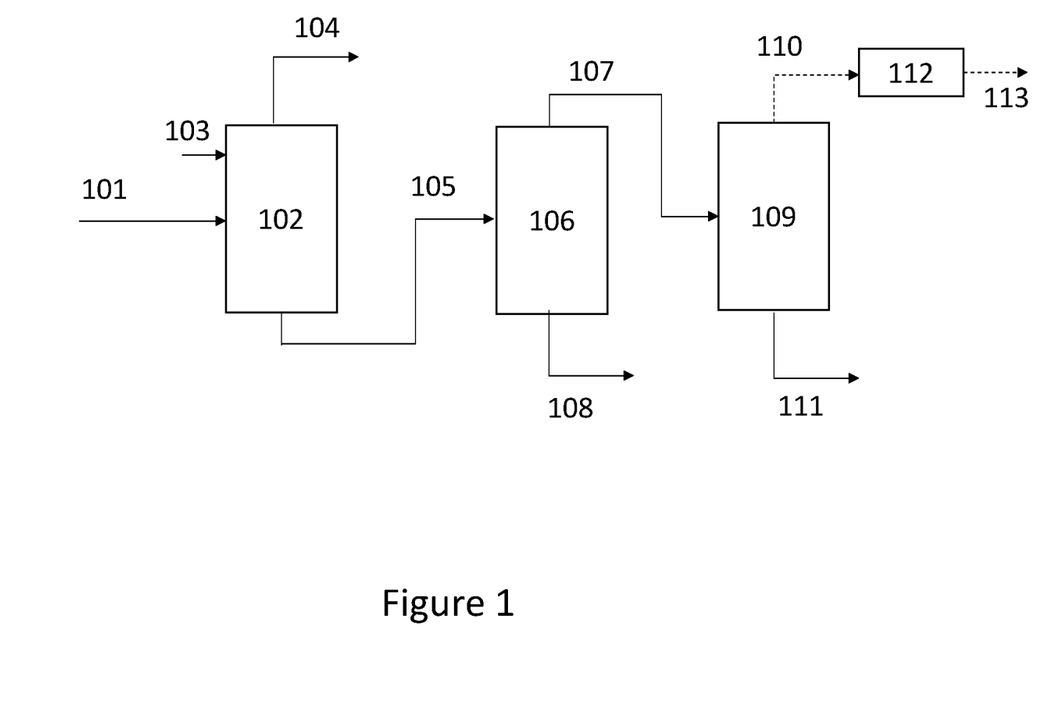
FIGS. 1 through 3 are schematic diagrams of exemplary, but non-limiting, embodiments of the process for the separation of glycols as described herein.

In FIG. 1, a solvent-lean product stream 101 derived from a saccharide hydrogenolysis process, is provided to a first distillation column 102. In some embodiments, the solvent-lean product stream 101 may have been subjected to one or more processes to remove solvent from the saccharide hydrogenolysis process, in most cases water. Suitable steps to remove light compounds may also have been applied to this solvent-lean product stream 101. The solvent-lean product stream 101 comprises two or more C2 to C7 diols.

The solvent-lean product stream 101 comprising two or more C2 to C7 diols comprises 0.1 to 10 wt % of diols with atmospheric boiling points at least 10° C. higher than the first diol, calculated upon the total weight of C2 to C7 diols in the product stream. A feed comprising an extractant 103 is provided to the first distillation column 102 above the solvent-lean product stream 101.

The first distillation column 102 is operated to produce a first top stream 104 comprising a mixture comprising one or more C2 to C7 diols and a first bottoms stream 105 comprising a mixture comprising a first diol and the extractant.

The first top stream 104 is removed from the first distillation column 102 above the point at which the extractant 103 is provided to the first distillation column. In some embodiments, the first top stream may be subjected to one or more fractional distillation steps in order to produce desired products as pure product streams.

The first bottoms stream 105 is provided to a second distillation column 106 in which the first diol and diols with atmospheric boiling points at least 10° C. higher than the first diol is distilled to provide a second top stream 107. A second bottoms stream 108 is removed. The second bottoms stream 108 comprises a used extractant stream. At least a first portion of the second bottoms stream may then be recycled to the first distillation column 102 as at least a portion of the extractant. In some embodiments, the second top stream 107 may comprise about 95 wt % of the first diol. In other embodiments, the second top stream 107 may comprise about 99 wt % of the first diol. By varying the amount of the first diol in the second top stream 107, the temperature in the bottom of the second distillation column 106 may be controlled such that a lower energy consumption is realized for the process.

The second top stream 107 is then supplied as a feed to a third distillation column 109. A stream comprising a high purity diol is removed as a third top stream 110 and a third bottoms stream 111 is removed. The third bottoms stream 111 comprising high boiling by-products may be further processed or recovered.

In this embodiment, the third top stream 110 is optionally further purified in a finishing process 112, to remove any type of light impurities/light degradation products formed in the separation process and provide an on-spec diol product stream 113. The on-spec diol product stream 113 may meet fibre grade specifics, including UV spec and product purity levels. In some embodiments, the product purity is 99.9 wt % of the first diol.

Figure 2:
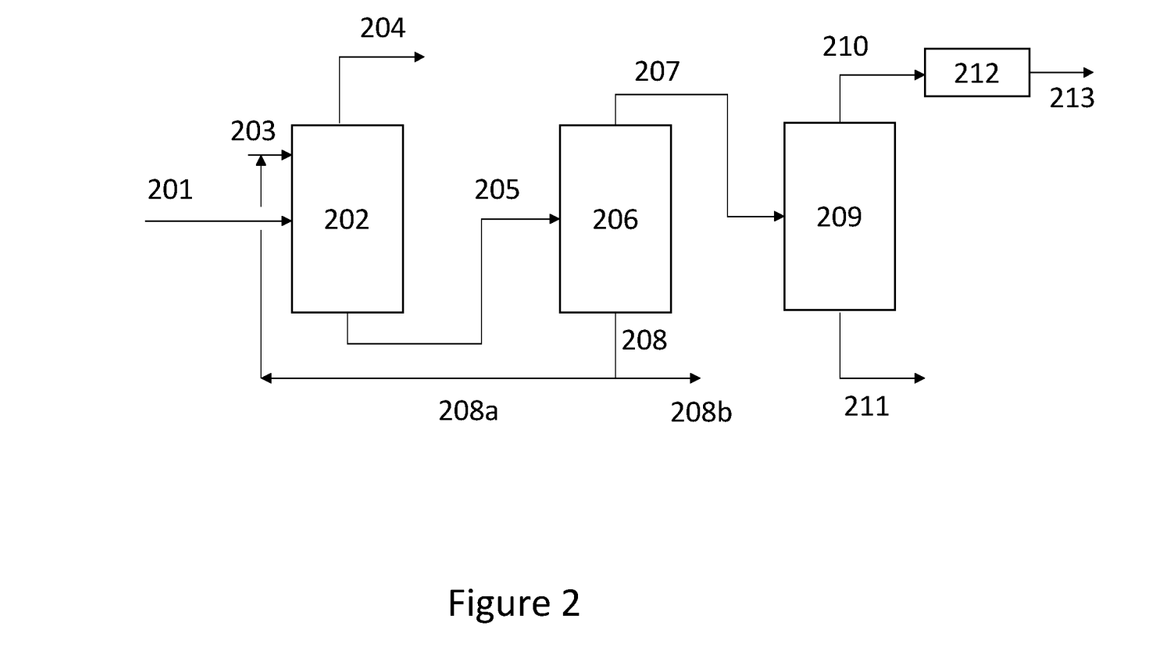

In FIG. 2, a solvent-lean product stream 201 derived from a saccharide hydrogenolysis process, is provided to a first distillation column 202. In some embodiments, the solvent-lean product stream 201 may have been subjected to one or more processes to remove solvent from the saccharide hydrogenolysis process, in most cases water. Suitable steps to remove light compounds may also have been applied to this solvent-lean product stream 201. The solvent-lean product stream 201 comprises two or more C2 to C7 diols. A feed comprising an extractant 203 is provided to the first distillation column 202 above the solvent-lean product stream 201.

The first distillation column 202 is operated to produce a first top stream 204 comprising a mixture comprising one or more C2 to C7 diols and a first bottoms stream 205 comprising a mixture comprising a first diol and the extractant.

The first top stream 204 is removed from the first distillation column 202 above the point at which the extractant 203 is provided to the first distillation column. In some embodiments, the first top stream may be subjected to one or more fractional distillation steps in order to produce desired products as pure product streams.

The first bottoms stream 205 is provided to a second distillation column 206 in which the first diol and diols with atmospheric boiling points at least 10° C. higher than the first diol is distilled to provide a second top stream 207. A second bottoms stream 208 is also provided. A first portion 208a may be recycled back to the first distillation column 202 and a second portion 208b may be bled off. This bleed stream 208b can be disposed of or at least partly recovered by separation and recycling to the first distillation column 202. In some embodiments, the second top stream 207 may comprise about 95 wt % of the first diol. In other embodiments, the second top stream 207 may comprise about 99 wt % of the first diol.

By varying the amount of the first diol in the second top stream 207, the temperature in the bottom of the second distillation column 206 may be controlled such that a lower energy consumption is realized for the process.

The second top stream 207 is then supplied as a feed to a third distillation column 209. A stream comprising a high purity diol is removed as a third top stream 210 and a third bottoms stream 211 is removed. The third bottoms stream 211 comprising high boiling by-products may be further processed or recovered.

In this embodiment, the third top stream 210 is further purified in a finishing process 212, to remove any type of light impurities/light degradation products formed in the separation process and provide an on-spec diol product stream 213. The on-spec diol product stream 213 may meet fibre grade specifics, including UV spec and product purity levels. In some embodiments, the product purity is 99.9 wt % of the first diol.

Figure 3:
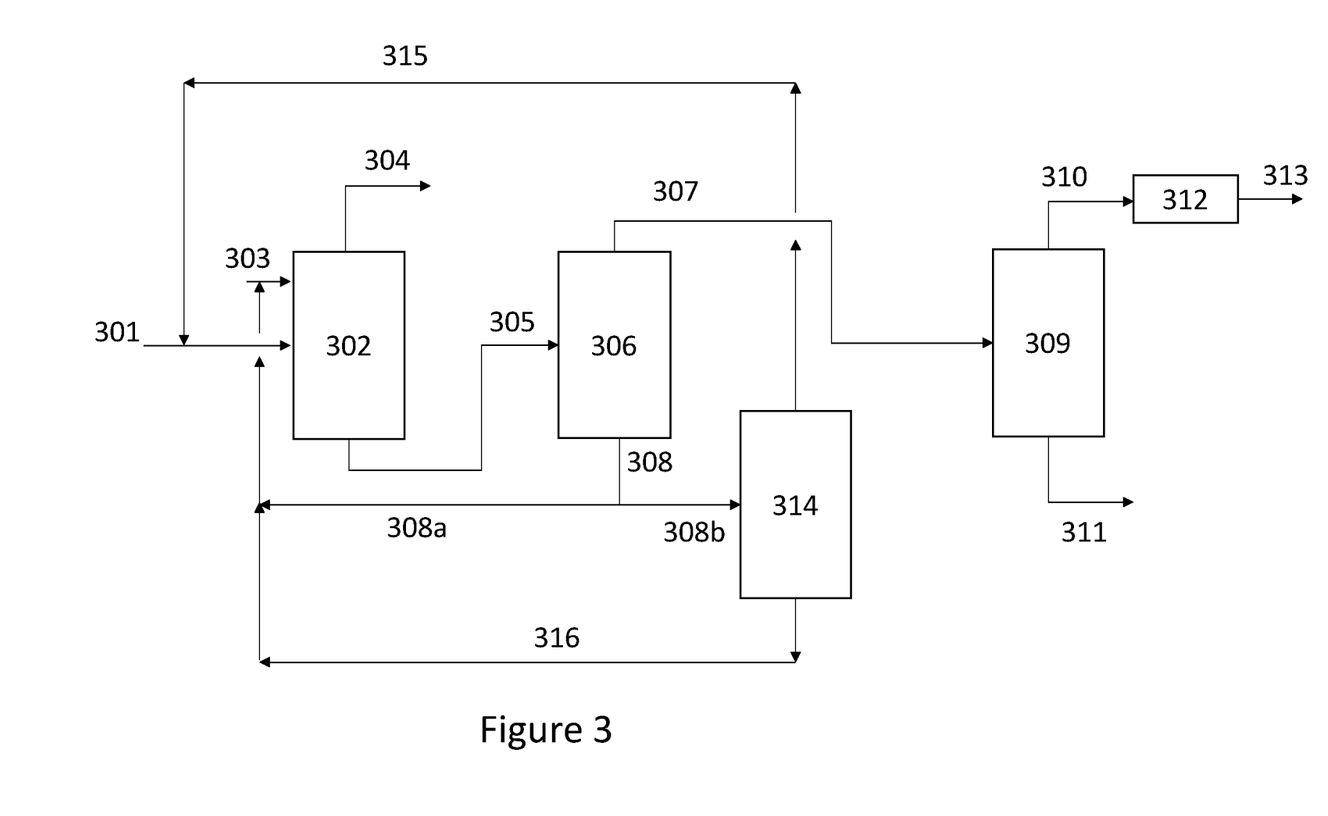

A further embodiment is shown in FIG. 3. The second portion 308b of the second bottoms stream may be provided to a fourth distillation column 314. The fourth distillation column 314 provides a fourth top stream 315 and a fourth bottoms stream 316.

The fourth top stream 315 comprises at least the first diol and may be recycled to the first distillation column 302. The fourth bottoms stream 316 may comprise the used extractant and may be recycled to the first distillation column 302.

Potential heat integrations may be used in both embodiments to increase the energy efficiency of the systems.

EXAMPLES

Embodiments will be further illustrated by the following, non-limiting examples.

Heavy Components Separation Prior to Extractive Distillation

Aspen Plus software was used to model removal of light components from a MEG mixture obtained by hydrogenolysis of saccharides.

After removal of light components, product streams comprising two or more C2 to C7 diols were obtained, which streams comprised 0.1 to 10 wt % of diols with atmospheric boiling points at least 10° C. higher than MEG, calculated upon the total weight of C2 to C7 diols in the product stream. Especially product streams comprising 0.1 to 10 wt % 1,2 hexanediol (1,2-HDO), calculated upon the total weight of C2 to C7 diols in the product stream, were obtained.

The composition of the mixture of glycols and tungstate catalyst, after removal of water, is given in Table A, expressed as flow rates for the components under consideration.

TABLE A

Mixed glycols stream, after removal of water

| Component | Flow rate (tonne/year) |
|---|---|
| MEG | 863 |
| MPG | 85 |
| 1,2-butanediol | 14 |
| 1,2-hexanediol | 38 |
| Glycerol | 18 |
| Erythritol | 87 |
| Sorbitol | 105 |
| Others | 64 |
| Total flow | 1273 |

Heavy components were removed from the mixed glycol stream shown in Table A. Results of flashing (using a single tray) are depicted in Tables B, C and D. The temperature and the pressure were varied, to evaluate the recovery of MEG, 1,2-HDO and glycerol.

TABLE B

Single-tray flash results at 50 mbar

| Temperature | Mass recovery overtop (m/m) | | | Heating duty |
|---|---|---|---|---|
| (deg. C.) | MEG | 1,2-HDO | Glycerol | (kW) |
| 140 | 0.937 | 0.951 | 0.257 | 26.61 |
| 145 | 0.955 | 0.969 | 0.351 | 27.67 |
| 150 | 0.967 | 0.979 | 0.447 | 28.53 |
| 155 | 0.976 | 0.986 | 0.540 | 29.27 |
| 160 | 0.981 | 0.990 | 0.624 | 29.95 |
| 165 | 0.986 | 0.993 | 0.698 | 30.58 |
| 170 | 0.989 | 0.994 | 0.760 | 31.20 |
| 175 | 0.991 | 0.996 | 0.812 | 31.81 |
| 180 | 0.993 | 0.997 | 0.854 | 32.42 |
| 185 | 0.994 | 0.998 | 0.888 | 33.06 |
| 190 | 0.996 | 0.998 | 0.914 | 33.70 |
| 195 | 0.997 | 0.999 | 0.935 | 34.35 |
| 200 | 0.997 | 0.999 | 0.951 | 34.98 |

P = 50 mbar

TABLE C

Single-tray flash results at 100 mbar

| Temperature | Mass recovery overtop (m/m) | | | Heating duty |
|---|---|---|---|---|
| (deg. C.) | MEG | 1,2-HDO | Glycerol | (kW) |
| 140 | 0.667 | 0.631 | 0.045 | 18.44 |
| 145 | 0.824 | 0.830 | 0.107 | 23.50 |
| 150 | 0.891 | 0.908 | 0.182 | 25.92 |
| 155 | 0.926 | 0.945 | 0.269 | 27.45 |
| 160 | 0.947 | 0.965 | 0.362 | 28.58 |
| 165 | 0.961 | 0.976 | 0.456 | 29.49 |
| 170 | 0.971 | 0.983 | 0.545 | 30.28 |
| 175 | 0.977 | 0.988 | 0.626 | 30.99 |
| 180 | 0.982 | 0.991 | 0.696 | 31.66 |
| 185 | 0.986 | 0.993 | 0.756 | 32.31 |
| 190 | 0.989 | 0.995 | 0.807 | 32.95 |
| 195 | 0.991 | 0.996 | 0.848 | 33.59 |
| 200 | 0.993 | 0.997 | 0.882 | 34.24 |

P = 100 mbar

TABLE D

Single-tray flash results at 200 mbar

| Temperature | Mass recovery overtop (m/m) | | | Heating duty |
|---|---|---|---|---|
| (deg. C.) | MEG | 1,2-HDO | Glycerol | (kW) |
| 140 | 0.000 | 0.000 | 0.000 | −1.27 |
| 145 | 0.000 | 0.000 | 0.000 | −0.70 |
| 150 | 0.014 | 0.010 | 0.000 | 0.31 |
| 155 | 0.492 | 0.445 | 0.028 | 14.75 |
| 160 | 0.756 | 0.760 | 0.090 | 22.77 |
| 165 | 0.853 | 0.875 | 0.166 | 26.03 |
| 170 | 0.902 | 0.927 | 0.252 | 27.92 |
| 175 | 0.931 | 0.953 | 0.344 | 29.24 |
| 180 | 0.949 | 0.969 | 0.436 | 30.28 |
| 185 | 0.961 | 0.978 | 0.524 | 31.16 |
| 190 | 0.970 | 0.984 | 0.604 | 31.94 |
| 195 | 0.977 | 0.989 | 0.675 | 32.66 |
| 200 | 0.982 | 0.991 | 0.736 | 33.35 |

P = 200 mbar

The results in Tables B to D show that 98% (m/m) MEG was recovered at 160° C. at 50 mbar, at 180° C. at 100 mbar, and at 200° C. at 200 mbar. The corresponding 1,2-HDO recoveries were 99%, indicating a lack of separation between MEG and 1,2-HDO under flashing conditions. Glycerol recovery increased with increasing pressure.

In a next set of experiments using Aspen Plus software, heavy components were removed from the mixed glycol stream shown in Table A using a limited number of trays.

Results of separation using 3 to 9 trays are depicted in Tables E to N. The number of trays, the reflux ratio, and the temperature were varied, to evaluate the recovery of MEG, 1,2-HDO and glycerol.

TABLE E

Multiple tray separation at 0.1 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.1 | 2 | 102 | 0.0223 | 0.871 | 0.830 | 27.04 |
| 5 | 0.1 | 3 | 104 | 0.00379 | 0.862 | 0.738 | 26.55 |
| 7 | 0.1 | 4 | 106 | 0.000853 | 0.855 | 0.662 | 26.29 |
| 9 | 0.1 | 5 | 108 | 0.000197 | 0.847 | 0.606 | 26.06 |

P condenser = 100 mbara
T reboiler = 150 deg. C.

TABLE F

Multiple tray separation at 0.25 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.25 | 2 | 102 | 0.0203 | 0.871 | 0.828 | 30.96 |
| 5 | 0.25 | 3 | 104 | 0.00167 | 0.862 | 0.710 | 30.39 |
| 7 | 0.25 | 4 | 106 | 0.000172 | 0.855 | 0.613 | 30.09 |
| 9 | 0.25 | 5 | 108 | 1.78E−05 | 0.847 | 0.545 | 29.80 |

P condenser = 100 mbara
T reboiler = 150 deg. C.

TABLE G

Multiple tray separation at 0.5 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.5 | 2 | 102 | 0.0178 | 0.871 | 0.825 | 37.49 |
| 5 | 0.5 | 3 | 104 | 0.000876 | 0.862 | 0.676 | 36.80 |
| 7 | 0.5 | 4 | 106 | 5.40E−05 | 0.855 | 0.543 | 36.42 |
| 9 | 0.5 | 5 | 108 | 3.33E−06 | 0.848 | 0.452 | 36.07 |

P condenser = 100 mbara
T reboiler = 150 deg. C.

TABLE H

Multiple tray separation at 0.1 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.1 | 2 | 102 | 0.0593 | 0.977 | 0.979 | 31.14 |
| 5 | 0.1 | 3 | 104 | 0.00458 | 0.975 | 0.963 | 30.67 |
| 7 | 0.1 | 4 | 106 | 0.00101 | 0.975 | 0.941 | 30.62 |
| 9 | 0.1 | 5 | 108 | 0.000240 | 0.975 | 0.909 | 30.60 |

P condenser = 100 mbara
T reboiler = 180 deg. C.

TABLE J

Multiple tray separation at 0.25 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.25 | 2 | 102 | 0.0567 | 0.976 | 0.979 | 35.56 |
| 5 | 0.25 | 3 | 104 | 0.002015 | 0.975 | 0.958 | 35.01 |
| 7 | 0.25 | 4 | 106 | 2.04E−04 | 0.976 | 0.928 | 34.96 |
| 9 | 0.25 | 5 | 108 | 2.20E−05 | 0.977 | 0.882 | 34.95 |

P condenser = 100 mbara
T reboiler = 180 deg. C.

TABLE K

Multiple tray separation at 0.5 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.5 | 2 | 102 | 0.0536504 | 0.9764968 | 0.9783408 | 42.91 |
| 5 | 0.5 | 3 | 104 | 0.0010532 | 0.9757101 | 0.9511388 | 42.259 |
| 7 | 0.5 | 4 | 106 | 6.42E−05 | 0.976522 | 0.9045 | 42.223 |
| 9 | 0.5 | 5 | 108 | 4.20E−06 | 0.9784 | 0.8303 | 42.219 |

P condenser = 100 mbara
T reboiler = 180 deg. C.

TABLE L

Multiple tray separation at 0.5 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.1 | 2 | 62 | 0.0262 | 0.948 | 0.937 | 28.88 |
| 5 | 0.1 | 3 | 64 | 0.00303 | 0.947 | 0.888 | 28.59 |
| 7 | 0.1 | 4 | 66 | 0.000562 | 0.948 | 0.830 | 28.55 |
| 9 | 0.1 | 5 | 68 | 0.000106 | 0.949 | 0.765 | 28.54 |

P condenser = 60 mbara
T reboiler = 150 deg. C.

TABLE M

Multiple tray separation at 0.25 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.25 | 2 | 62 | 0.0242 | 0.948 | 0.936 | 33.21 |
| 5 | 0.25 | 3 | 64 | 0.00131 | 0.948 | 0.872 | 32.88 |
| 7 | 0.25 | 4 | 66 | 0.000111 | 0.949 | 0.791 | 32.84 |
| 9 | 0.25 | 5 | 68 | 9.44E−06 | 0.951 | 0.704 | 32.83 |

P condenser = 60 mbara
T reboiler = 150 deg. C.

TABLE N

Multiple tray separation at 0.5 reflux ratio

| Trays (N) | Reflux Ratio | Feed tray | P re-boiler | Mass recovery over top (m/m) | | | Re-boiler duty |
|---|---|---|---|---|---|---|---|
| (#) | (w/w) | (#) | (mbar) | Glycerol | MEG | 12HDO | (kW) |
| 3 | 0.5 | 2 | 62 | 0.0217 | 0.948 | 0.934 | 40.44 |
| 5 | 0.5 | 3 | 64 | 0.000677 | 0.948 | 0.851 | 40.05 |
| 7 | 0.5 | 4 | 66 | 3.46E−05 | 0.951 | 0.731 | 40.02 |
| 9 | 0.5 | 5 | 68 | 1.75E−06 | 0.954 | 0.603 | 40.00 |

P condenser = 60 mbara
T reboiler = 150 deg. C.

Heavy Components Separation—Comparable Examples

In the examples in WO2017050847 no 1,2 HDO, or only 0.01 wt % 1,2 HDO, was present in the feed to the extractive distillation column. Components such as 1,2 hexanediol were separated in a first distillation column together with high boiling components in the bottoms stream of the first distillation column, before extractive distillation. The required distillation set up and conditions for such separation was investigated in the following Comparable examples using Aspen Plus software.

Heavy components as well as 1,2-HDO were removed from the mixed glycol stream shown in Table A. Results of distillation are depicted in Tables P, Q and R. The number of trays used in the distillation and the reflux ratio were varied, to evaluate the recovery of MEG, 1,2-HDO and glycerol.

TABLE P

Multiple-tray distillation at 1.2 reflux ratio

| Trays (N) | Reflux Ratio | Feed tray | P re-boiler | Mass recovery overtop (m/m) | | | Re-boiler duty |
|---|---|---|---|---|---|---|---|
| (#) | (w/w) | (#) | (mbar) | Glycerol | MEG | 12HDO | (kW) |
| 10 | 1.2 | 5 | 109 | 0 | 0.986 | 0.589 | 62.62 |
| 20 | 1.2 | 10 | 119 | 0 | 0.995 | 0.166 | 62.45 |
| 30 | 1.2 | 15 | 129 | 0 | 0.992 | 0.101 | 62.22 |
| 40 | 1.2 | 20 | 139 | 0 | 0.988 | 0.0795 | 61.97 |
| 50 | 1.2 | 25 | 149 | 0 | 0.984 | 0.0679 | 61.716 |
| 60 | 1.2 | 30 | 159 | 0 | 0.979 | 0.0606 | 61.449 |
| 70 | 1.2 | 35 | 169 | 0 | 0.974 | 0.0558 | 61.17 |

P condenser = 100 mbara
T reboiler = 180 deg. C.

TABLE Q

Multiple-tray distillation at 1.8 reflux ratio

| Trays (N) | Reflux Ratio | Feed tray | P re-boiler | Mass recovery overtop (m/m) | | | Re-boiler duty |
|---|---|---|---|---|---|---|---|
| (#) | (w/w) | (#) | (mbar) | Glycerol | MEG | 12HDO | (kW) |
| 10 | 1.8 | 5 | 109 | 0 | 0.989 | 0.513 | 80.08 |
| 20 | 1.8 | 10 | 119 | 0 | 0.997 | 0.082 | 79.83 |
| 30 | 1.8 | 15 | 129 | 0 | 0.994 | 0.029 | 79.51 |
| 40 | 1.8 | 20 | 139 | 0 | 0.990 | 0.0142 | 79.19 |
| 50 | 1.8 | 25 | 149 | 0 | 0.986 | 0.0075 | 78.863 |
| 60 | 1.8 | 30 | 159 | 0 | 0.981 | 0.0041 | 78.517 |
| 70 | 1.8 | 35 | 169 | 0 | 0.975 | 0.0023 | 78.155 |

P condenser = 100 mbara
T reboiler = 180 deg. C.

TABLE R

Multiple-tray distillation at 2.4 reflux ratio

| Trays (N) (#) | Reflux Ratio (w/w) | Feed tray (#) | P re-boiler (mbar) | Mass recovery overtop (m/m) | | | Re-boiler duty (kW) |
|---|---|---|---|---|---|---|---|
| | | | | Glycerol | MEG | 12HDO | |
| 10 | 2.4 | 5 | 109 | 0 | 0.990 | 0.467 | 97.54 |
| 20 | 2.4 | 10 | 119 | 0 | 0.998 | 0.050 | 97.20 |
| 30 | 2.4 | 15 | 129 | 0 | 0.995 | 0.011 | 96.81 |
| 40 | 2.4 | 20 | 139 | 0 | 0.990 | 0.0038 | 96.43 |
| 50 | 2.4 | 25 | 149 | 0 | 0.986 | 0.0013 | 96.021 |
| 60 | 2.4 | 30 | 159 | 0 | 0.981 | 0.0005 | 95.598 |
| 70 | 2.4 | 35 | 169 | 0 | 0.976 | 0.0002 | 95.154 |

P condenser = 100 mbara
T reboiler = 180 deg. C.

From the results in Tables P, Q and R is clear that almost complete separation of 1,2-HDO in this first distillation column requires a relatively large amount of energy. It also requires a relatively large number of trays and relatively large equipment.

Example 1—Mixed Glycols Isolation

Glycol mixtures were obtained by conversion of glucose as described in WO2018/064245. A total of 165.2 kg reactor effluent was obtained from a reactor feed including 19.6 kg glucose and 145.6 kg water in total.

Water and light components like traces of methanol and ethanol were removed in ten separate batches by rotary evaporation, which mimics flashing. A liquid fraction, mostly water, of 144.9 kg was collected and discarded leaving an organic fraction.

A mixed glycols fraction of 16.9 kg was obtained by subsequent rotary evaporation of the organic fraction. Mass balances of the ten individual batches indicate a loss of about 1.7 kg glycols with the water fraction, while the water content in the mixed glycols fraction could be as high as 2.4 kg water. These mass balances indicate a total yield of 14.5 kg of glycols recovered from the 16.9 kg mixed glycols fraction obtained (89.5% w of total mixed glycols generated).

Also obtained from the subsequent rotary evaporation of the mixed glycols fraction is a residual fraction of 3.4 kg comprising sorbitol, erythritol, glycerol and residual catalyst. The residual fraction has not been analysed in further detail.

TABLE 1

Mass balance of mixed glycols preparation and isolation

| | Reactor feed (kg) | Rotary evaporation water fraction (kg) | Rotary evaporation mixed glycols (kg) | Rotary evaporation heavy residue (kg) |
|---|---|---|---|---|
| Glucose | 19.6 | | | |
| Glycols | | 1.7 | 14.5 | |
| Water | 145.6 | 143.2 | 2.4 | |
| Polyols | | | | 3.4 |

The composition of the mixed glycols fraction has been analyzed by GC analysis, while the glycerol fraction was measured by LC analysis (Table 2—Feed). This mixed-glycols fraction was used as feed for Example 2, extractive distillation.

Example 2—Extractive Distillation

A first 2-inch glass double-wall distillation column was used for extractive distillation, with glycerol as extractant. The first column had three sections of approximately 167 cm height each. The top section was empty, while the middle and bottom sections were filled with Sulzer Mellapak Y-500 Hastelloy, approximately 140 cm total height each. The feed position was at ⅔ from the top, in between the two packed sections. The extractant feed entry was from the top of the first column. Height equivalent of a theoretical plate (HETP) was estimated at 22 cm.

A second 2-inch glass double-wall distillation column was used for ethylene glycol recovery and extractant recycling. The second column also had three sections of approximately 167 cm height each. The top section was empty, while the middle and bottom sections were equipped with Sigma-Aldrich Pro-Pak distillation packing. The middle section packing has a height of 20 cm, while the packing height of the bottom was 10 cm. The feed position was at ⅔ from the top, in between the two packed sections. HETP was estimated at 22 cm.

The first distillation column was operated at 231 mbar pressure, measured at the top of the column, a condenser temperature of 132 deg. C. and a reboiler liquid temperature of 180 deg. C. The mixed glycols feed flow rate was 50 g/h and the glycerol feed flow rate was 130 g/h, resulting in a top product flow rate of 6 g/h and a bottom product flow rate of 178 g/h. Water was fed into the reboiler at a flow rate of 0.5 g/h. The top reflux flow rate was gradually reduced over time, from 350 g/h to 32 g/h, representing a gradual decline in reflux ratio.

The second distillation column was operated at 91 mbar pressure, measured at the top of the column, a condenser temperature of 125 deg. C. and a reboiler liquid temperature of 202 deg. C. The feed to the second distillation column is the bottom product of the first distillation column, at a flow rate of 178 g/h, resulting in a top flow rate of 43 g/h and a bottom extractant flow rate of 134 g/h. Water was fed into the reboiler at a flow rate of 0.5 g/h. The top reflux flow rate was 25 g/h.

The compositions of the top product in the first distillation column and the top product of the second distillation column is given in Table 2.

TABLE 2

Compositions from Example 2

| Component | Feed [g/kg] | Top C-1 [g/kg] | Top C-2 [g/kg] |
|---|---|---|---|
| Ethylene glycol | 808.7 | 364.4 | 994.7 |
| Propylene glycol | 46.7 | 446.9 | 0.0 |
| 1,2-butanediol | 31.1 | 186.0 | 0.0 |
| 1,2-hexanediol | 10.6 | 0.0 | 6.5 |
| 2,3-pentanediol isomers | 7.5 | 14.1 | 0.0 |
| 2,3-butanediol isomers | 4.2 | 16.7 | 0.0 |
| x,y-hexanediol isomers | 2.8 | 5.0 | 0.0 |
| Cyclic diol 1 | 2.3 | 3.5 | 0.0 |
| glycerol | 2.0 | 0.0 | 0.0 |
| 2,5-hexanediol | 1.9 | 0.0 | <0.5 |
| 1,2-pentanediol | 1.8 | 2.7 | 0.0 |
| Cyclic diol 2 | 1.5 | 2.5 | 0.0 |
| Isosorbide | 1.3 | 0.0 | 0.0 |
| Total | 922 | 1042 | 998 |

The MEG obtained in Table 1 is not yet on specification, as too much 1,2-hexanediol is present. 1,2-hexanediol can easily be separated from MEG by conventional distillation, given the widely separated boiling points and the absence of an azeotrope.

The foregoing description, for purpose of explanation, has been described with reference to specific embodiments. However, the illustrative discussions above are not intended to be exhaustive or to limit embodiments of the disclosed subject matter to the precise forms disclosed. Many modifications and variations are possible in view of the above teachings. The embodiments were chosen and described in order to explain the principles of embodiments of the disclosed subject matter and their practical applications, to thereby enable others skilled in the art to utilize those embodiments as well as various embodiments with various modifications as may be suited to the particular use contemplated.

We claim:

1. A process for the production of a high purity first diol, selected from the group consisting of C2 to C7 diols from a product stream comprising two or more C2 to C7 diols, said process comprising the steps of:
   (i) providing the product stream to a first distillation column;
   (ii) providing an extractant selected from the group of C3 to C6 sugar alcohols and mixtures thereof to the first distillation column;
   (iii) operating the first distillation column at a temperature in the range of from 50 to 250° C. and a pressure in the range of from 0.1 to 400 kPa to obtain a first bottoms stream comprising at least a first diol and the extractant and a first top stream comprising a mixture comprising one or more C2 to C7 diols;
   (iv) providing the first bottoms stream to a second distillation column operating at a temperature in the range of from 50 to 250° C. and a pressure in the range of from 0.1 to 400 kPa to obtain a second top stream comprising the first diol and diols with atmospheric boiling points at least 10° C. higher than the first diol, and
   (v) providing the second top stream to a third distillation column to obtain a third top stream comprising the first diol in a purity higher than 99.5% by weight, wherein the product stream comprises 0.1 to 10 wt % of diols with atmospheric boiling points at least 10° C. higher than the first diol, calculated upon the total weight of C2 to C7 diols in the product stream.

2. The process according to claim 1, wherein prior to step (i) the product stream is subjected to rotary evaporation, flashing, and/or by separation using 1 to 10 trays, or 2 to 9 trays, or 3 to 5 trays, to remove high boiling components.

3. The process according to claim 1, wherein the first diol is MEG and the product stream comprises at least MEG and 1,2-BDO, wherein the product stream provided to step (i) has a weight ratio of MEG: 1,2-BDO of at least 5:1.

4. The process according to claim 1, wherein the first diol is MPG and the product stream comprises at least MPG and 2,3-pentanediol.

5. The process according to claim 1, wherein the product stream is, or is derived from, a product stream of a saccharide hydrogenolysis process, and wherein one or more sugar alcohols, or glycerol, is present in the product stream used in step (i).

6. The process according to claim 1, wherein the product stream comprises a solvent and prior to step (i) the solvent is removed from the product stream to provide a solvent-lean product stream, wherein the solvent may be water or a C1 to C6 alcohol or polyalcohol or mixtures thereof.

7. The process according to claim 6, wherein the product stream comprises at least MEG and 1,2-BDO and a solvent and prior to step (i) the solvent is removed from the product stream to provide a solvent-lean product stream.

8. The process according to claim 1, wherein a second bottoms stream comprising a used extractant stream is also obtained in step (iv), and wherein at least a first portion of the second bottoms stream comprising the used extractant is recycled to the first distillation column as at least a portion of the extractant.

9. The process according claim 1, wherein the extractant is added in an amount such that the weight ratio of the extractant to the product is at least 0.25:1 and at most 10:1 based on the overall weight of the feed/mixture.

10. The process according claim 1, wherein at least a second portion of the second bottoms stream comprising the used extractant and the at least first diol is provided to a fourth distillation column to obtain a fourth top stream comprising the first diol and a fourth bottoms stream comprising the used extractant, both of which are recycled to the first distillation column.

11. The process according to claim 1, wherein a finishing section is added to the top of the third distillation column above the point at which the high purity first diol stream is obtained, in order to remove any type of light impurities/light degradation products formed in the separation process, including by hydrogenation.

* * * * *